United States Patent
Chen et al.

(10) Patent No.: US 10,695,005 B2
(45) Date of Patent: Jun. 30, 2020

(54) NON-INVASIVE BLOOD SUGAR MEASURING METHOD AND FINGERTIP MEASURING PROBE

(71) Applicants: Guilin Medicine Electronic Technology Co., Ltd., Guilin, Guangxi Zhuang Autonomous Region (CN); Guilin University of Electronic Technology, Guilin, Guangxi Zhuang Autonomous Region (CN)

(72) Inventors: Zhencheng Chen, Guangxi Zhuang Autonomous Region (CN); Jianming Zhu, Guangxi Zhuang Autonomous Region (CN); Yongbo Liang, Guangxi Zhuang Autonomous Region (CN); Shimin Yin, Guangxi Zhuang Autonomous Region (CN); Guocheng Han, Guangxi Zhuang Autonomous Region (CN); Biao Xu, Guangxi Zhuang Autonomous Region (CN); Yang Zhang, Guangxi Zhuang Autonomous Region (CN)

(73) Assignees: Guilin Medicine Electronic Technology Co., Ltd., Guilin (CN); Guilin University of Electronic Technology, Guilin (CN)

(*) Notice: Subject to any disclaimer, the term of this patent is extended or adjusted under 35 U.S.C. 154(b) by 840 days.

(21) Appl. No.: 14/929,729

(22) Filed: Nov. 2, 2015

(65) Prior Publication Data
US 2016/0256114 A1 Sep. 8, 2016

(30) Foreign Application Priority Data
Mar. 2, 2015 (CN) .......................... 2015 1 0092412

(51) Int. Cl.
*A61B 5/00* (2006.01)
*A61B 5/1455* (2006.01)
(Continued)

(52) U.S. Cl.
CPC .............. *A61B 5/7267* (2013.01); *A61B 5/01* (2013.01); *A61B 5/14532* (2013.01);
(Continued)

(58) Field of Classification Search
CPC . A61B 5/1455; A61B 5/14532; A61B 5/7267; A61B 5/01; A61B 5/4866
See application file for complete search history.

(56) References Cited

U.S. PATENT DOCUMENTS 5,204,532 A * 4/1993 Rosenthal .......... A61B 5/14532
600/322
5,553,616 A * 9/1996 Ham .................. A61B 5/14558
600/316

(Continued)

OTHER PUBLICATIONS

Office Action and Search Report for copending application CN 201510092412.7 and an English language Translation.
(Continued)

*Primary Examiner* — Eric F Winakur
(74) *Attorney, Agent, or Firm* — Ladas & Parry LLP (57) ABSTRACT

The present invention discloses a non-invasive blood glucose measurement method, applied to noninvasive blood glucose measuring instruments including measuring hosts and fingertip measuring probes, comprising pre-storing a random forest algorithm and a neural network prediction algorithm in the measuring host; measuring energy metabolism parameters of a fingertip of an individual to be measured and transmitting the parameters to the measuring host by the fingertip measuring probe; calling the random forest algorithm to predict the blood glucose type of the energy metabolism parameters of the fingertip of the individual to
(Continued)

be measured and calling the corresponding neural network prediction algorithm to calculate the blood glucose value of the fingertip of the individual to be measured by the measuring host. The present invention also provides a fingertip-measuring probe. The non-invasive blood glucose measurement method disclosed in the present invention can be applied to non-invasive measurement of blood glucose, parameters related to energy metabolism of human body, healthy parameters of angiocarpy, etc.

9 Claims, 9 Drawing Sheets

(51) Int. Cl.
| | | |
|---|---|---|
| *A61B 5/01* | (2006.01) | |
| *A61B 5/145* | (2006.01) | |
| *G06F 19/00* | (2018.01) | |
| *G16H 40/63* | (2018.01) | |
| *G16H 50/20* | (2018.01) | |
| *A61B 5/026* | (2006.01) | |
| *A61B 5/024* | (2006.01) | |

(52) U.S. Cl.
CPC .......... *A61B 5/4866* (2013.01); *A61B 5/6826* (2013.01); *A61B 5/7275* (2013.01); *G06F 19/32* (2013.01); *G16H 40/63* (2018.01); *G16H 50/20* (2018.01); *A61B 5/026* (2013.01); *A61B 5/02438* (2013.01); *A61B 5/14551* (2013.01); *A61B 5/4266* (2013.01)

(56) References Cited

U.S. PATENT DOCUMENTS

| | | | | |
|---|---|---|---|---|
| 6,788,965 | B2* | 9/2004 | Ruchti | A61B 5/14532 600/310 |
| 8,019,400 | B2* | 9/2011 | Diab | A61B 5/7246 600/323 |
| 2005/0192492 | A1 | 9/2005 | Cho et al. | |
| 2011/0230744 | A1* | 9/2011 | Ribas Ripoll | A61B 5/14532 600/365 |

OTHER PUBLICATIONS

Ma Jinz, et al.: Non-invasive blood glucose measuring apparatus based on energy metabolic conservation: Journal of Guilin University of Electronic Technology: vol. 35: No. 1: Oct. 15, 2014.
Random Forests for Non-invasive Blood Glucose Sensing with NIR and the Design of Experimental System: Feb. 28, 2015.

* cited by examiner

S301 — Define the energy metabolism parameters in the specimen data of the low blood sugar type, intermediate blood sugar type and high blood sugar type as the input parameters of the corresponding neutral network.

S302 — Define a minimally invasive blood sugar value as a calibration parameter and the minimally invasive blood sugar value, namely the calibration parameter, as the expected output value of the neutral network, and constructing an original model of a non-invasive blood sugar value estimation system.

S303 — Set the specimen parameter data of the original model and initialize the weight and the threshold, calculate the output of the hidden layer and the output layer, define the output of the output layer of each of the low blood sugar type, intermediate blood sugar type and high blood sugar type and the secondary error criteria function of the invasive blood sugar value as the control function, calculate the system's total error criteria function for the system to the plurality of training specimen data, gradually calculate the output error of nerve cells on each layer from the output layer, then adjust the weight and threshold of the output layer and the hidden layer in accordance with an error gradient descent method, then calculate the error of all specimens according to the adjusted weight and threshold such that the final output value of the modified corresponding neutral system approaches the expected output value.

S304 — When the error of the output result is within the allowed scope or reaches the maximum learning times, stop learning; otherwise, continue to learning of a new cycle.

NON-INVASIVE BLOOD SUGAR MEASURING METHOD AND FINGERTIP MEASURING PROBE

BACKGROUND OF THE INVENTION

1. Technical Field

The present invention belongs to the technical field of medical instruments, in particular to a non-invasive blood sugar measuring method and fingertip measuring probe based on the energy metabolic conservation of human body.

2. Description of Related Art

Blood sugar is a key medical indicator in the detection, diagnosis and treatment of diabetes, clinically detecting the blood sugar concentration of a patient to determine the insulin dose needed to be injected, thus effectively regulating the glucose metabolism, preventing deterioration of the diabetes and reducing occurrence of the complication. Therefore, the detection, quantification and monitoring of the blood sugar content is a necessary means of diabetes diagnosis and treatment.

Non-invasive blood sugar detection technology combines spectral analysis, electro osmosis, photoelectric detection techniques, electrochemical techniques, signal processing analysis, and other correlative theories. It is a cross technology covering knowledge of many subjects. The non-invasive blood sugar detection using non-spectrum analysis method mainly employs the reverse ionic osmosis technology or ultrasonic technology and uses the electrodes on the body surface to collect the glucose in the subcutaneous tissue liquid specimen and converts it into the blood sugar content. The first one who applied the non-spectra analysis method to the non-invasive blood sugar detection is American CygnusInc company. This company firstly obtained the approval of producing the wrist type non-invasive blood sugar instrument—Gluco Watch. In 2006, Liu Jian, etc. used the reverses iontophoresis technology to develop a non-invasive blood sugar detection prototype and made corresponding animal tests. The feasible analysis has certain reference values. According to the non-invasive blood sugar detection using the light spectrum analysis, a light source transmits a light signal; the light transmits the cuticle, epidermis, dermis, subcutaneous tissue, interstitial fluid and blood sugar; the sensors are disposed at different positions to detect the reflected light or the intensity of intensity of transmitted beam, which is compared with the intensity of reference beam to quantify the blood sugar value. In 1990, American Hutchinson used the rotation characteristics of the polarized light of glucose to measure the glucose concentration in the fluid of the chamber of eyeball, accordingly deduced the blood sugar concentration of the human body and obtained the related technology patents. In 1992, American Sandia Lab and the Medical College of University of New Mexico together researched a non-invasive blood sugar measurement sensor and made a success in 1995. Such method also has many problems when applied to detect the blood sugar values of the same or different patients at different times, such as the temperature influences, metabolite concentration, and light absorbency interference of other substances, which needed to be solved.

In conclusion, no simple and efficient non-invasive detection of blood sugar is disclosed yet.

BRIEF SUMMARY OF THE INVENTION

One of the objectives of the present invention is to provide a non-invasive blood sugar measuring method and a fingertip measuring probe based on energy metabolic conservation of the human body to keep stable relationship between the input signal and the measuring result.

The present invention provides a non-invasive blood glucose measurement method, applied to noninvasive blood glucose measuring instruments including measuring hosts and fingertip measuring probes, comprising pre-storing a random forest algorithm and a neural network prediction algorithm in the measuring host; measuring energy metabolism parameters of a fingertip of an individual to be measured and transmitting the parameters to the measuring host by the fingertip measuring probe; calling the random forest algorithm to predict the blood glucose type of the energy metabolism parameters of the fingertip of the individual to be measured and calling the corresponding neural network prediction algorithm to calculate the blood glucose value of the fingertip of the individual to be measured by the measuring host.

Furthermore, the random forest algorithm is preset with the low blood sugar type, intermediate blood sugar type and high blood sugar type; the low blood sugar type is corresponding to the low blood sugar neural network prediction algorithm. The intermediate blood sugar type is corresponding to the intermediate blood sugar type is corresponding to the intermediate blood sugar neural network prediction algorithm and the high blood sugar type is corresponding to the high blood sugar neural network prediction algorithm.

Furthermore, before the step of pre-storing the random forest algorithm and the neural network prediction algorithm in the measuring host, a step is comprised: measuring the energy metabolism parameters of a plurality of individual fingertips to obtain specimen data of the plurality of individuals by the fingertip measuring probe, each individual's specimen data containing different energy metabolism parameters of the fingertips thereof; employing the random forest algorithm to classify the specimen data of a plurality of individuals into low blood sugar type, intermediate blood sugar type and high blood sugar type through a computer; and, defining the energy metabolism parameters in the specimen data of the low blood sugar type, intermediate blood sugar type and high blood sugar type as the input parameters of the original models of the non-invasive blood sugar value estimation system to obtain the low blood sugar neutral network prediction algorithm, intermediate blood sugar neutral network prediction algorithm and high blood sugar neutral network prediction algorithm.

Furthermore, the step of employing the random forest algorithm to classify the specimen data of a plurality of individuals into low blood sugar type, intermediate blood sugar type and high blood sugar type through a computer specifically comprises: randomly selecting individual specimen data from a plurality of individual specimen data; splitting nodes of the selected individual specimen data and constructing a decision-making tree; repeating the above step to construct a plurality of decision-making trees to generate random forests; voting the decision-making tree in the random forests, and according to the voting result, classifying the plurality of individual specimen data into the low blood sugar type, intermediate blood sugar type and high blood sugar type.

Furthermore, the step of defining the energy metabolism parameters in the specimen data of the low blood sugar type, intermediate blood sugar type and high blood sugar type as the input parameters of the original models of the non-invasive blood sugar value estimation system to obtain the low blood sugar neutral network prediction algorithm, intermediate blood sugar neutral network prediction algorithm and high blood sugar neutral network prediction algorithm specifically comprises: defining the energy metabolism parameters in the specimen data of the low blood sugar type, intermediate blood sugar type and high blood sugar type as the input parameters of the corresponding neutral network; defining a minimally invasive blood sugar value as a calibration parameter and the minimally invasive blood sugar value, namely the calibration parameter, as the expected output value of the neutral network, and constructing an original model of a non-invasive blood sugar value estimation system; setting the specimen parameter data of the original model and initialize the weight and the threshold, calculating the output of the hidden layer and the output layer, defining the output of the output layer of each of the low blood sugar type, intermediate blood sugar type and high blood sugar type and the secondary error criteria function of the invasive blood sugar value as the control function, calculating the system's total error criteria function for the system to the plurality of training specimen data, gradually calculating the output error of nerve cells on each layer from the output layer, then adjusting the weight and threshold of the output layer and the hidden layer in accordance with an error gradient descent method, then calculating the error of all specimens according to the adjusted weight and threshold such that the final output value of the modified corresponding neutral system approaches the expected output value; when the error of the output result is within the allowed scope or reaches the maximum learning times, stopping learning; otherwise, continuing to learning of a new cycle.

Furthermore, the calculation formula of the original model is: Y=purelin (T*tansig (W*X+$\theta_i$))+$\theta_1$; X is the input parameter of the neutral network prediction algorithm; W and T are weights; $\theta_i$ and $\theta_1$ are thresholds; and Y is the final output value of the corresponding neutral network prediction algorithm.

Furthermore, the calculation formula of the neutral network predication algorithm is:

$$\begin{cases} Y_L = purelin(T_L * \tansig(W_L * X_L + \theta_{iL})) + \theta_{1L} \\ Y_M = purelin(T_M * \tansig(W_M * X_M + \theta_{iM})) + \theta_{1M} \\ Y_H = purelin(T_H * \tansig(W_H * X_H + \theta_{iH})) + \theta_{1H} \end{cases}$$

wherein, $X_L$, $X_M$ and $X_H$ respectively are the input parameters of the low, intermediate and high blood sugar neutral network prediction algorithms; $W_L$, $W_M$, $W_H$, $T_L$, $T_M$, $T_H$ are the weights of the low, intermediate and high blood sugar neutral network prediction algorithms; $\theta_{1L}$, $\theta_{1M}$, $\theta_{1H}$, $\theta_{iL}$, $\theta_{iM}$, $\theta_{iH}$ are thresholds of the low, intermediate and high blood sugar neutral network prediction algorithms; $Y_L$, $Y_M$, $Y_H$ are the final output values of the low, intermediate and high blood sugar neutral network prediction algorithms.

Furthermore, the step of measuring the energy metabolism parameters of the fingertip of the individual to be measured and transmitting the parameters to the measuring host by the fingertip measuring probe comprises: measuring the difference $\Delta T$, humidity difference $\Delta RH$ and radiation temperature difference $\Delta RAD$ of the fingertip surface of the human body and the environment, the blood oxygen saturation difference Spo2 of the fingertip of the human body, the blood flow velocity By, and the pulse rate value Hr by the fingertip measuring probe; calculating $\Delta T$, $\Delta RH$ and $\Delta RAD$ to obtain the basic metabolism rate BMR by the fingertip measuring probe; transmitting the energy metabolism parameters including $\Delta T$, $\Delta RH$, $\Delta RAD$ and BMR to the measuring host by the fingertip measuring probe.

Furthermore, the step of calling the random forest algorithm to predict the blood sugar type of the energy metabolism parameter of the fingertip of the individual to be measured and calling the corresponding neutral network prediction algorithm to calculate the blood sugar value of the fingertip of the individual to be measured by the measuring host comprises: calling a plurality of decision-making tree models in the constructed random forest algorithm to judge the blood sugar type of the energy metabolism parameter; according to the voting result of every decision-making tree and in accordance with the principle that the minority is subordinate to the majority, classifying the individual specimen data into the low blood sugar type, or intermediate blood sugar type or high blood sugar type; according to the classification result, calling the corresponding neutral network prediction algorithm pre-stored in the host to calculate and obtain the invasive blood sugar value of the fingertip of the individual to be measured.

The present invention also comprises a fingertip measuring probe, comprising a first circuit board and a second circuit board; a temperature-humidity sensor, disposed at the upper surface of the second circuit board for measuring the temperature and humidity on the finger surface; a radiation temperature sensor, disposed at the lower surface of the second circuit board for measuring the radiation temperature of the finger surface; an environmental temperature-humidity sensor, disposed at the lower surface of the second circuit board for measuring the environmental temperature and humidity; a photoelectric receiver disposed at the upper surface of the second circuit board, a light-emitting diode disposed on the upper surface of the first circuit board, the light-emitting diode emitting light rays which penetrate through the fingertip and then are received by the photoelectric receiver.

Furthermore, the fingertip measuring probe also comprises an upper holding portion, a lower holding portion, a connecting flat wire, and the connecting flat wire is connected between the upper holding portion and the lower holding portion.

Furthermore, the fingertip-measuring probe also comprises a communication cable, which penetrates through the lower holding portion and is connected with the second circuit board.

The non-invasive blood sugar measuring method and fingertip measuring probe provided by the present invention can be applied to the non-invasive detection of the parameters related to the energy metabolism and cardiovascular health of the human body, and can keep the relationship between the input signal and the measuring result stable.

DETAILED DESCRIPTION OF THE INVENTION

The embodiments of the present invention are described in detail with reference to the attached drawings. It shall be noted that, the technical characteristics or combinations thereof described in the embodiments shall be not regarded to be isolated, and they can be combined to achieve better technical effects. In the attached drawings of the following embodiments, the same marks in the drawings represent the same characteristics or parts, and can be applied to different embodiments.

Figure 1:
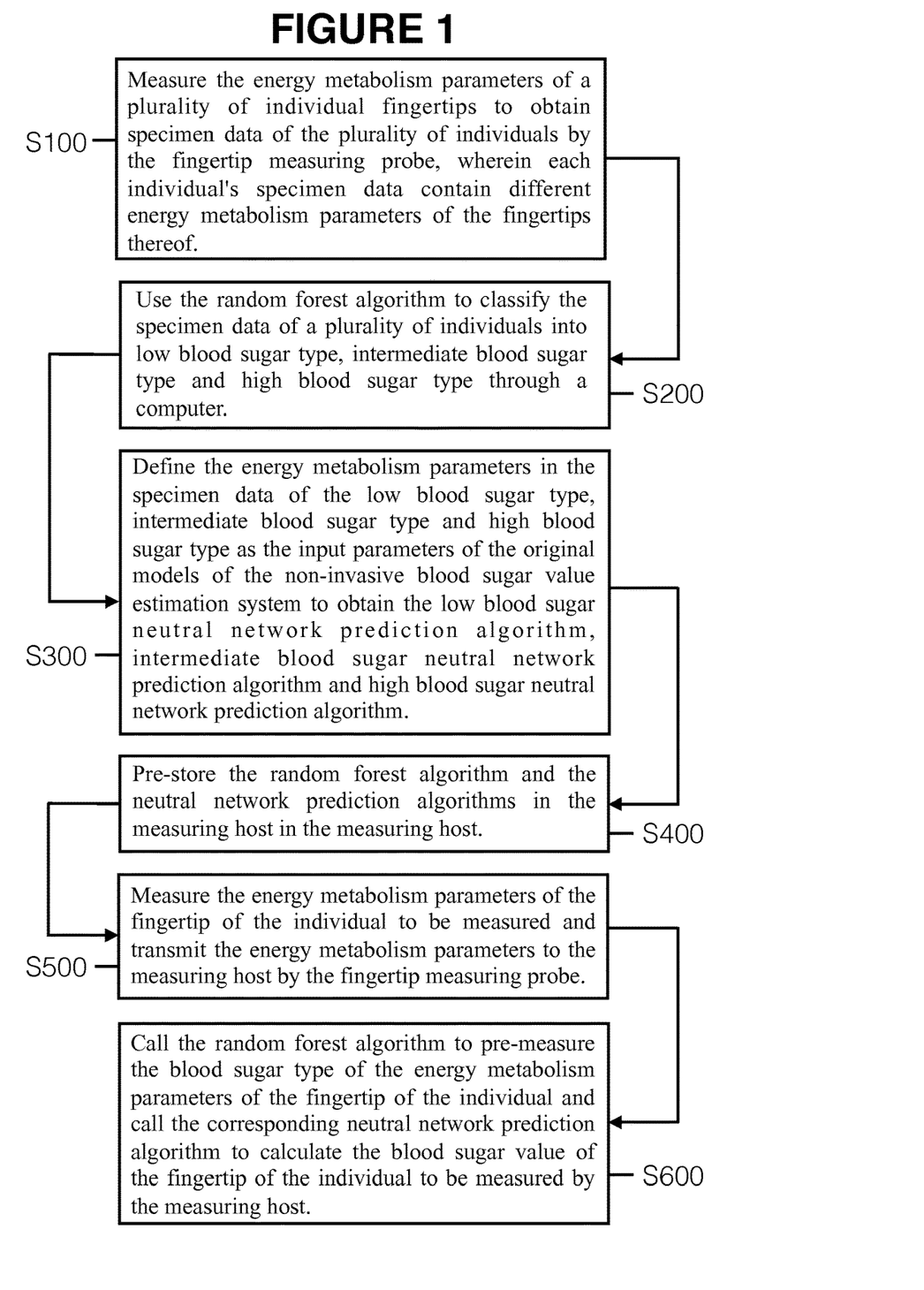
FIG. 1 is a flowchart of the non-invasive blood sugar measuring method of the present invention.

FIG. 1 is a flowchart of the non-invasive blood sugar measuring method of the present invention.

A non-invasive blood sugar measuring method of the present invention, applied to non-invasive blood sugar measuring instruments including measuring hosts and fingertip measuring probes, comprises step S100, step S200, step 300, step S400, step S500 and step S600. Each step is described in detail below.

Step 100: Measure the energy metabolism parameters of a plurality of individual fingertips to obtain specimen data of the plurality of individuals by the fingertip measuring probe, wherein each individual's specimen data containing different energy metabolism parameters of the fingertips thereof.

Step 200: Employ the random forest algorithm to classify the specimen data of a plurality of individuals into low blood sugar type, intermediate blood sugar type and high blood sugar type through a computer.

Figure 2:
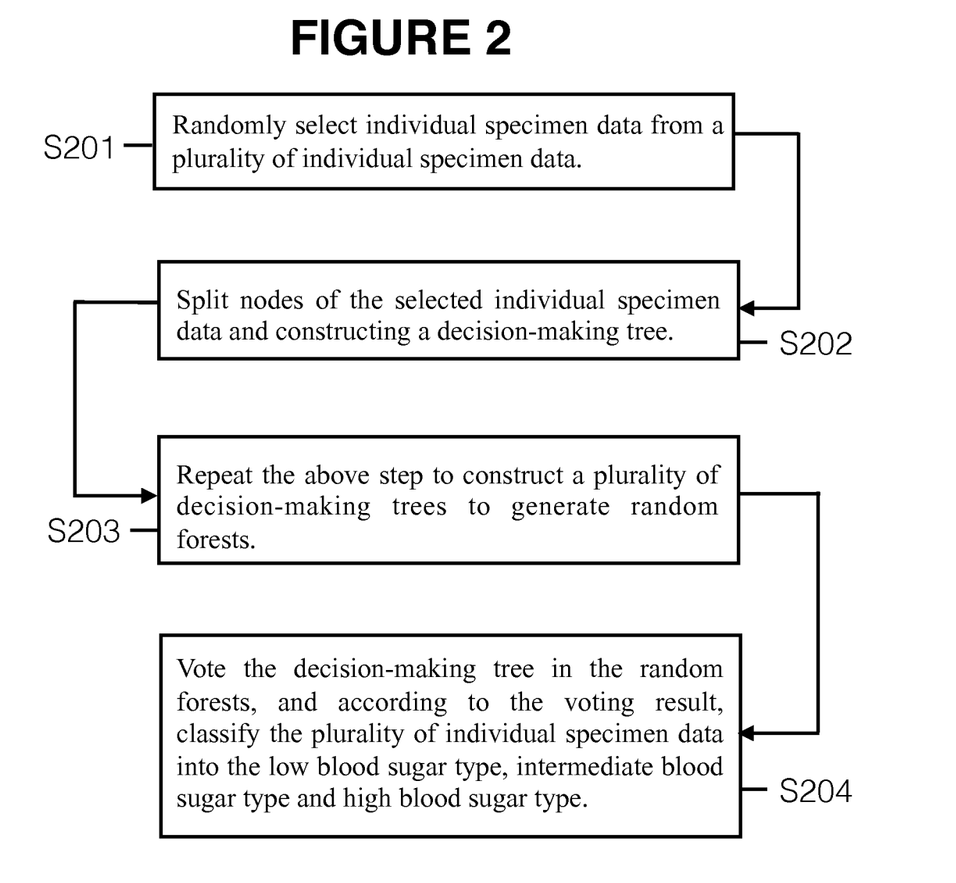
FIG. 2 is a specific flowchart of step S200.

FIG. 2 is a specific flowchart of step S200.

Step S200 specifically comprises:

Step S201, randomly select individual specimen data from a plurality of individual specimen data.

Step S202, split nodes of the selected individual specimen data and construct a decision-making tree.

Step S203, repeat the above step to construct a plurality of decision-making trees to generate random forests.

Step S204, vote the decision-making tree in the random forests, and according to the voting result, classify the plurality of individual specimen data into the low blood sugar type, intermediate blood sugar type and high blood sugar type.

Step S300, define the energy metabolism parameters in the specimen data of the low blood sugar type, intermediate blood sugar type and high blood sugar type as the input parameters of the original models of the non-invasive blood sugar value estimation system to obtain the low blood sugar neutral network prediction algorithm, intermediate blood sugar neutral network prediction algorithm and high blood sugar neutral network prediction algorithm.

In this embodiment, to generate the branch of every decision-making tree, the attribute is selected according to the splitting algorithm. The splitting algorithm may be CLS algorithm, C4.5 algorithm or CART algorithm. When CART algorithm is used, Gini indicator can be used to select the splitting attribute and classify the measurement data. The attribute selected using the Gini indicator is relatively uniform, does not generate the problem of bias, and is applicable to specimen sets with complicated and variable attributes and parameters.

Figure 3:
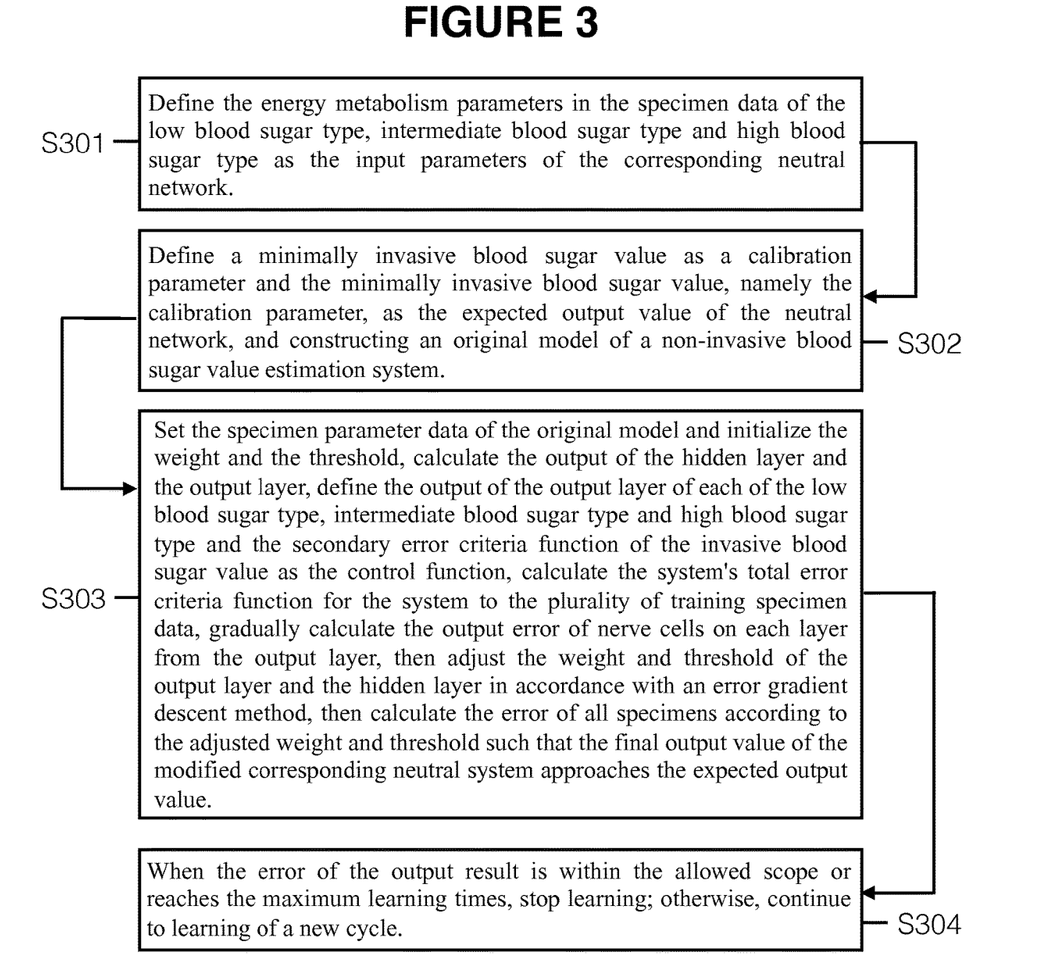
FIG. 3 is a specific flowchart of step S300.

FIG. 3 is a specific flowchart of step S300.

Step S300 specifically comprises:

Step S301, define the energy metabolism parameters in the specimen data of the low blood sugar type, intermediate blood sugar type and high blood sugar type as the input parameters of the corresponding neutral network.

Step S302, Define a minimally invasive blood sugar value as a calibration parameter and the minimally invasive blood sugar value, namely the calibration parameter, as the expected output value of the neutral network, and construct an original model of a non-invasive blood sugar value estimation system. In this embodiment, the calculation formula of the original module is Y=purelin (T*tansig (W*X+ $\theta_i$))+$\theta_1$; X is the input parameter of the neutral network prediction algorithm; W and T are weights; $\theta_i$ and $\theta_1$ are thresholds; and Y is the final output value of the corresponding neutral network prediction algorithm.

Step 303, set the specimen parameter data of the original model and initialize the weight and the threshold, calculate the output of the hidden layer and the output layer, define the output of the output layer of each of the low blood sugar type, intermediate blood sugar type and high blood sugar type and the secondary error criteria function of the invasive blood sugar value as the control function, calculate the system's total error criteria function for the system to the plurality of training specimen data, gradually calculate the output error of nerve cells on each layer from the output layer, then adjust the weight and threshold of the output layer and the hidden layer in accordance with an error gradient descent method, then calculate the error of all specimens according to the adjusted weight and threshold such that the final output value of the modified corresponding neutral system approaches the expected output value.

Step S304, when the error of the output result is within the allowed scope or reaches the maximum learning times, stop learning; otherwise, continue to learning of a new cycle.

At completion of steps S301-S304, obtain the following calculation formula of the neutral network prediction algorithm:

$$\begin{cases} Y_L = purelin(T_L * \tan sig(W_L * X_L + \theta_{iL})) + \theta_{1L} \\ Y_M = purelin(T_M * \tan sig(W_M * X_M + \theta_{iM})) + \theta_{1M} \\ Y_H = purelin(T_H * \tan sig(W_H * X_H + \theta_{iH})) + \theta_{1H} \end{cases}$$

wherein, $X_L$, $X_M$ and $X_H$ respectively are the input parameters of the low, intermediate and high blood sugar neutral network prediction algorithms; $W_L$, $W_M$, $W_H$, $T_L$, $T_M$, $T_H$ are the weights of the low, intermediate and high blood sugar neutral network prediction algorithms; $\theta_{1L}$, $\theta_{1M}$, $\theta_{1H}$, $\theta_{iL}$, $\theta_{iM}$, $\theta_{iH}$ are thresholds of the low, intermediate and high blood sugar neutral network prediction algorithms; $Y_L$, $Y_M$, $Y_H$ are the final output values of the low, intermediate and high blood sugar neutral network prediction algorithms.

Step S400, pre-store a random forest algorithm and a neural network prediction algorithm in the measuring host.

In this embodiment, the random forest algorithm is preset with the low blood sugar type, intermediate blood sugar type and high blood sugar type; the low blood sugar type is corresponding to the low blood sugar neural network prediction algorithm; the intermediate blood sugar type is corresponding to the intermediate blood sugar type is corresponding to the intermediate blood sugar neural network prediction algorithm; and the high blood sugar type is corresponding to the high blood sugar neural network prediction algorithm.

Step S500, measure the energy metabolism parameters of the fingertip of the individual to be measured and transmit the energy metabolism parameters to the measuring host by the fingertip-measuring probe.

Figure 4:
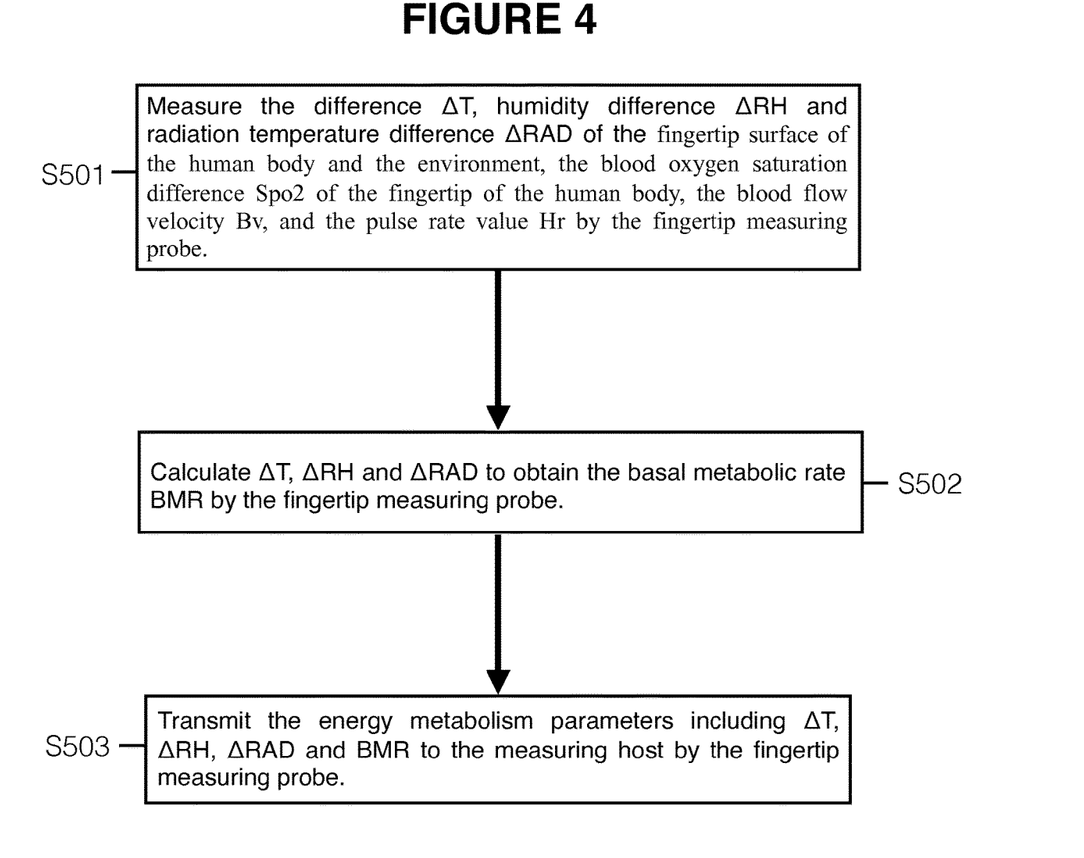
FIG. 4 is a specific flowchart of step S500.

FIG. 4 is a specific flowchart of step S500.

Step S500 specifically comprises:

Step S501, measure the difference ΔT, humidity difference ΔRH and radiation temperature difference ΔRAD of the fingertip surface of the human body and the environment, the blood oxygen saturation difference Spo2 of the fingertip of the human body, the blood flow velocity Bv, and the pulse rate value Hr by the fingertip measuring probe;

Step S502, calculate ΔT, ΔRH and ΔRAD to obtain the basic metabolism rate BMR by the fingertip measuring probe;

Step S503, transmit the energy metabolism parameters including ΔT, ΔRH, ΔRAD and BMR to the measuring host by the fingertip-measuring probe.

Step 600, call the random forest algorithm to pre-measure the blood sugar type of the energy metabolism parameters of the fingertip of the individual and call the corresponding neutral network prediction algorithm to calculate the blood sugar value of the fingertip of the individual to be measured by the measuring host.

In this embodiment, the final output result of the algorithm is obtained by the final majority voting method using the decision-making trees. The randomly constructed N decision-making sub-trees classify a certain test specimen; the results of all sub-trees are collected; in the principle that the minority is subordinate to the majority, the classification result with the most votes is used as the final output result of the algorithm. Thus, the classification of the blood sugar values of the individuals is complete.

In the present invention, due to the complication of the blood sugar adjustment process, in particular the difference in the biological information of the low blood sugar value group, intermediate blood sugar value group and high blood sugar value group, it is decided to use the random forest method to classify the blood sugar of different groups after testing. Simply speaking, a forest consisting of many decision-making trees is built randomly, and the decision-making trees of the random forest are not correlated. After the forest is obtained, when a new input specimen enters, every decision-making tree in the forest judges the type of the input specimen, then judges which type is selected most and next predicts the type of the specimen. The random forest algorithm mainly includes the generation and voting processes of the decision-making trees.

First, construct the decision-making trees:

To construct N decision-making trees, it is needed to generate corresponding quantity of training sets. Generating N training sub-sets from the original training set relates to the technology of sampling with replacement (bagging sampling technology). The purpose of doing so is to prevent the decision-making trees in the forest to generate the partial optimal solution. N decision-making trees are generated to form a "forest". Every decision-making tree grows without pruning treatment. When every tree grows the branches, the attribute is selected according to a certain splitting rule. The calculation indicators of the node-splitting rule are also not the same.

In the present invention, the splitting rules capable of being employed include CLS (Concept Learning System) algorithm, C4.5 algorithm, and CART (Classification And Regression Tree) algorithm.

CLS algorithm is the early decision-making tree generation algorithm. In the CLS algorithm, the node splitting process is random. First, randomly select one attribute from all attributes of a data set as a root node, and start to split from this attribute. The splitting process depends on the set value of the attribute, and the number of the value scopes of the attribute is corresponding to the number of the branches. The execution of the algorithm is ended until a leave node is generated. The rule of generating the leave node is as follows: the current data set is null, or all specimens in this data set belong to the same type.

C4.5 algorithm is based on ID3 algorithm. ID3 algorithm abides by a fixed rule when selecting the attribute. This rule is as follows: the attributes are compared through introducing information entropies, and the attribute as the splitting node is determined through comparing the size of the information entropies. This algorithm starts from the calculation of the information entropy, calculating the information gain ratio of every attribute.

The calculation process of the information gain is as follows:

Calculate the information entropy of the node $$Info(D) = -\sum_{i=1}^{IN} P_i \log_2 P_i$$

Classify the expectation information needed for the specimen classification of D on the basis of A, wherein the formulas are below:

$$Info_A(D) = \sum_{i=1}^{v} \left[\left(\frac{|D_i|}{D}\right) * Info(D_i)\right]$$

The above two formulas can obtain the information gain. The definition formula is:

Gain(A)=Info(D)−InfoA(D)

Gain (A) represents reduction of the expectation of the information need caused by the value of A, namely the information gain.

The calculation process of the information gain ratio is as follows:

$$SplitInfo_A(D) = -\sum_{i=1}^{v} \left[\left(\frac{|D_i|}{D}\right) * \log_2\left(\frac{|D_i|}{D}\right)\right]$$

Wherein, v represents the number of the values of the attribute A.

The calculation process of the information gain ratio is:

$$GainRatio(A) = \frac{Gain(A)}{SplitInfo_A(D)}$$

Then, compare and select the attribute for splitting according to the size of the information gain. For example, the maximum attribute is used as the node-splitting attribute.

CART algorithm divides the values of the splitting attributes into two sub-sets, then starting from those two sub-sets, calculates the Gini indicators decided by the training set, next employs the binary recursion mode to divide the current training set into two sub-sets, thus generate a sub-tree with left and right two branches. When the node is split, this algorithm uses the Gini indicator to measure data classification.

Calculate the Gini coefficient of the specimen $$Gini(S) = 1 - \sum_{i=1}^{m} P_i^2$$

Wherein, Pi represents the probability of the Cj in the specimen set S.

Calculate the Gini coefficient of every division

If S is divided into two sub-sets S1 and S2, the Gini coefficient of this division is $$Gini_{split}(s) = \frac{|S_1|}{S} Gini(S_1) + \frac{|S_2|}{S} Gini(S_2)$$

Then, select the attribute corresponding to the splitting mode with the minimum ginisplit (S) as the node-splitting attribute.

2.2 Random Selection of Random Characteristic Variable

When the random forest splits the node, not all attributes participate in the calculation of the attribute indicator, but several certain attributes are randomly selected to participant in the comparison, and the participating attributes are called random characteristic variables.

2.3 Formation of the Forest and Execution of the Algorithm

Repeat the above steps to build a great number of decision-making trees, and then a random forest is generated. The final output result of the algorithm is obtained by the majority vote method.

Figure 5:
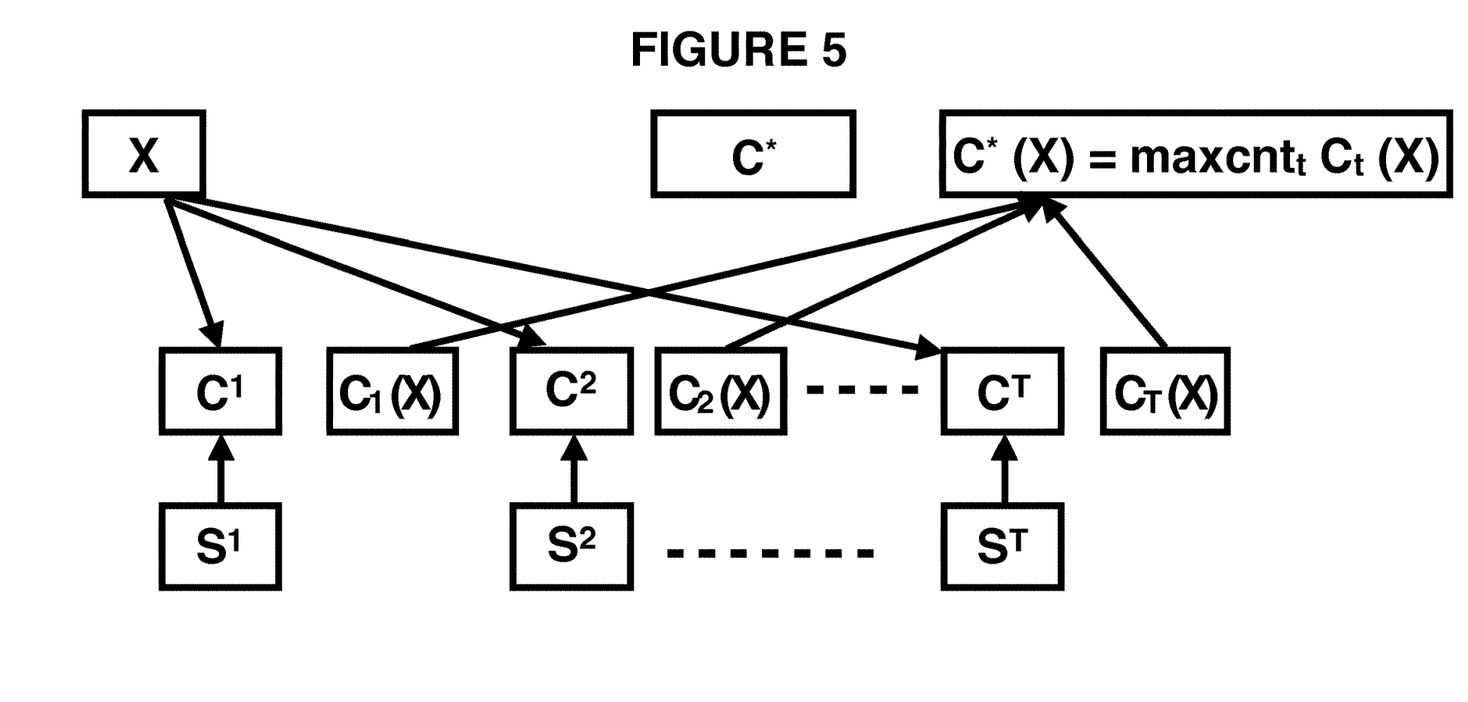
FIG. 5 is a schematic view of the voting process of the decision-making tree.

FIG. 5 is a schematic view of the voting process of the decision-making tree.

In the present invention, the voting formula of the decision-making tree is:

$$C_p = \mathrm{argmax}_c \left( \frac{1}{n_{tree}} \sum_{i=1}^{n_{tree}} I\left( \frac{n_{n_{i,c}}}{n_{l_i}} \right) \right)$$

Note: nc is the total number of the type;

In this embodiment, the beneficial effects of using the random forest method to classify the blood sugar values of the individuals are as follows:

Generate a high-accuracy classifier through combination of thoughts.

Conveniently and quickly process a great number of input variables.

Evaluate the characteristic importance of the data set characteristics to finish characteristic selection.

When evaluating the characteristic importance, also provide a method for testing the relevance among the characteristics.

Well balance the error to solve the unbalanced classification problem.

The OOB data generated when constructing the random forest can well implement the estimation without bias on the classifier error.

The structure of the random forest is conveniently obtained and the calculation learning is very quick.

Well tolerate the abnormalities and noise interference and effectively restrain the generation of the over-fitting problem of the classifier.

Therefore, the embodiment of the present invention uses the very good non-linear modeling algorithm of the random forest to well to realize the complicated parameter calculation of the human body physiological research field, and in comparison with the support vector machine, K-means clustering, decision-making tree, Bayesian classification and other classification algorithms, is more applicable to the classification of the non-invasive blood sugar measurement parameters.

Figure 6:
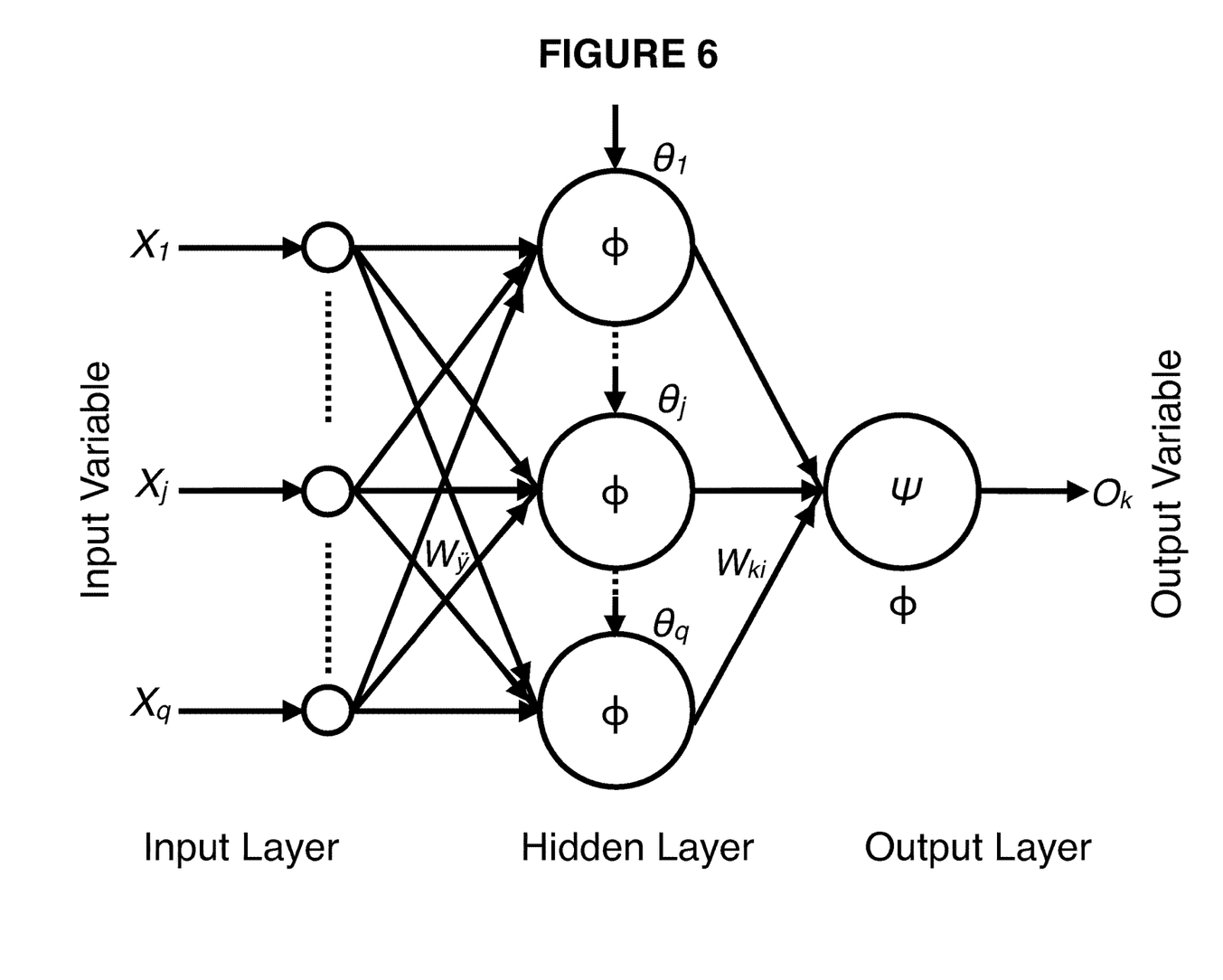
FIG. 6 is a topological structure diagram of the neutral network prediction algorithm of the present invention.

Specifically speaking, the neutral network in this embodiment of the present invention is a reverse transmission network. FIG. 6 is a topological structure diagram of the neutral network prediction algorithm of the present invention.

The most important application of the reverse transmission neutral network is functional approximation. The core is the error reverse transmission to correct the weight and threshold of each node, such that the error function descends along the negative gradient. The reverse transmission neutral network comprises three layers of nodes, namely input nodes, hidden nodes and output nodes. First, create a cascade forward reverse transmission network, and then implement training by using the non-invasive blood sugar characteristic value and the invasive blood sugar value as input and the measured real value as the output. Randomly select the training and predication data, randomly determining the initial weight matrix W (0), implement reverse correction until running out of all learning data. The neutral network training function is of randomness, so the accuracy obtained through training is different every time. The complied prediction function is used for stimulation; the absolute error between the stimulation value and the real value is used as the condition; and the while sentence is used as to circularly train the data to obtain the network with the highest accuracy. The trained network includes the weight and the deviation. Multiply the weight of the hidden layer by the input, add the deviation of the hidden layer, then apply the transmission function of the hidden layer, and then the obtained result is input of the output layer. Likewise, multiply the weight of the output layer by the input of the output layer, add the deviation of the output layer, and then apply the transmission function of the output layer to obtain output. Thus, the accuracy of the trained value is greatly improved.

Node of the Hidden Layer:

$$\begin{cases} \text{Error formula} & \delta_i = f_t(net_1) * \sum_i \delta_i T_{1i} \\ \text{Weight correction} & w^{(p)}(i,j) = w^{(p-1)}(i,j) + \eta \delta_i x(j) \\ \text{Threshold correction} & \theta_1^{(p)} = \theta_i^{(p-1)} + \eta \delta_i \end{cases}$$

In the formula, xj input the node input

Node of the Output Layer $$\begin{cases} \text{Error formula} & \delta_1 = (t_1 - o_1) * f'(net_1) \\ \text{Weight correction} & T^{(p)}(1,i) = T^{(p-1)}(1,i) + \eta \delta_1 y(j) \\ \text{Threshold correction} & \theta_i^{(p)} = \theta_i^{(p-1)} + \eta \delta_i \end{cases}$$

In the formula, $$y_i = f\left(\sum_j w_{ij} x_j - \theta_i\right)$$

represents hidden node output;

$$o_1 = f\left(\sum_i T_{ij} y_i - \theta_1\right)$$

represents the output node output $$net_i = \sum_j W(i,j) * x_j - \theta_i, \; net_i = \sum_j T(1,i) * y_i - \theta_1$$

W is the array of the hidden node weight; θi is the threshold error of the hidden node; T is the array of the output node weight; and θ1 is the threshold error of the output node.

$$\sum_1 \delta_1 T_{1i}$$

in δi represents that the error δ1 of the output layer node 1 is obtained by reverse transmission of T1i to the hidden node i.

the neutral network input array is X; the finally obtained hidden layer weight array is W, the deviation array is θi; the output layer weight array is T, the deviation array is θ1; and the finally obtained results of the three types of blood sugar are:

$$\begin{cases} Y_L = purelin(T_L * \tansig(W_L * X_L + \theta_{iL})) + \theta_{1L} \\ Y_M = purelin(T_M * \tansig(W_M * X_M + \theta_{iM})) + \theta_{1M} \\ Y_H = purelin(T_H * \tansig(W_H * X_H + \theta_H)) + \theta_{1H} \end{cases}$$

The hemoglobin content measurement principle of the present invention is as follows:

Human tissues are different in the absorption degree of the near-infrared light. The absorption degree of the oxyhemoglobin and deoxyhemoglobin of the human varies to the maximum extent at 660 nm and 940 nm. At 805 nm, the absorption degree of the oxyhemoglobin and deoxyhemoglobin is the same. At 730 nm, the absorption degree of the deoxyhemoglobin is relatively low. At positions of those two wave lengths, the characteristics of the oxyhemoglobin and deoxyhemoglobin can be most reflected, and then according to the Lambert-Beer's Law, near-infrared light at 660 n, 730 nm, 805 nm and 940 nm are selected as the detection wave lengths.

$A = Ig(Io/It) + \lambda = Ig(1/T) + \lambda = k \times 1 \times c + \lambda.$

The physical meaning of the Lambert-Beer's Law: when a beam of parallel monochromatic light vertically passes through a certain uniform non-scattered light-absorbing substance, the absorbency A to the concentration c of the light-absorbing substance to the thickness d of the absorption layer is in positive ratio. However, the content of the oxyhemoglobin and the deoxyhemoglobin is measured through measuring the fingers. Fingers are not uniform non-scattered light-absorbing substances, so correction is needed. A constant needs to be added in the above formula $A = Ig(Io/It) + \lambda = Ig(1/T) + \lambda = k \times 1 \times c + \lambda.$ Wherein, A is the absorbency; I0 is the incident light intensity; It is the intensity of transmitted beam; T is the transmittancy (transmittance of light); k is the light-absorbing coefficient; 1 is the media thickness; c is the concentration of the light-absorbing substance; and λ is the correction constant.

Figure 7:
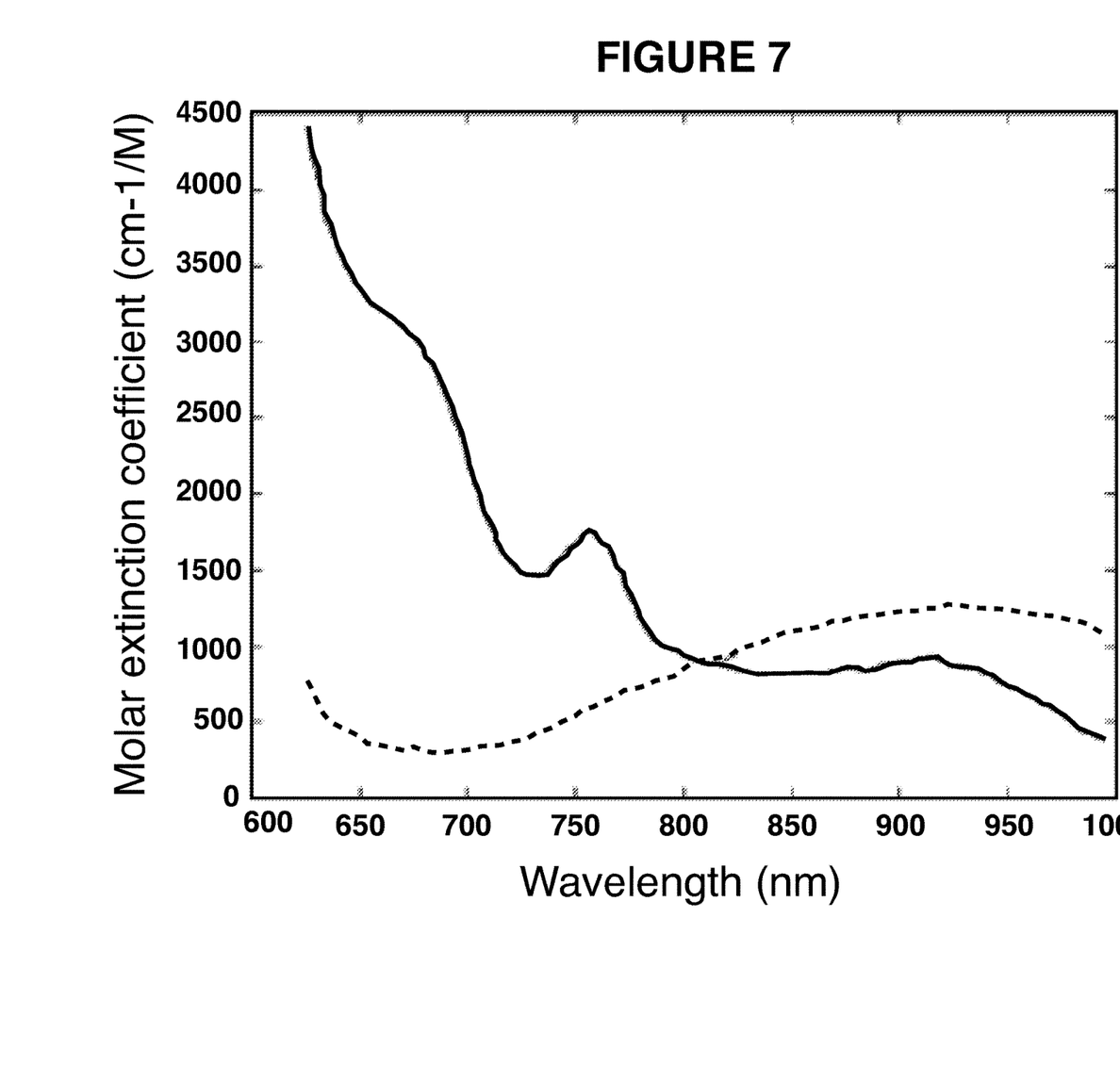
FIG. 7 is an absorbency characteristic diagram of hemoglobin.

FIG. 7 is an absorbency characteristic diagram of hemoglobin.

The full line is the absorption coefficient curve of the hemoglobin, and the dotted line is the absorption coefficient curve of the oxyhemoglobin.

According to the formula $A = k \times 1 \times c + \lambda$, four different formulas are obtained:

$$A^{660} = k_{Hbo_2}^{660} \times c_{Hbo_2} \times 1 + k_{Hb}^{660} \times c_{Hb} \times 1 + \lambda$$

$$A^{940} = k_{Hbo_2}^{940} \times c_{Hbo_2} \times 1 + k_{Hb}^{940} \times c_{Hb} \times 1 + \lambda$$

$$A^{730} = k_{Hbo_2}^{730} \times c_{Hbo_2} \times 1 + k_{Hb}^{730} \times c_{Hb} \times 1 + \lambda$$

$$A^{805} = k_{Hbo_2}^{805} \times c_{Hbo_2} \times 1 + k_{Hb}^{805} \times c_{Hb} \times 1 + \lambda$$

Figure 8:
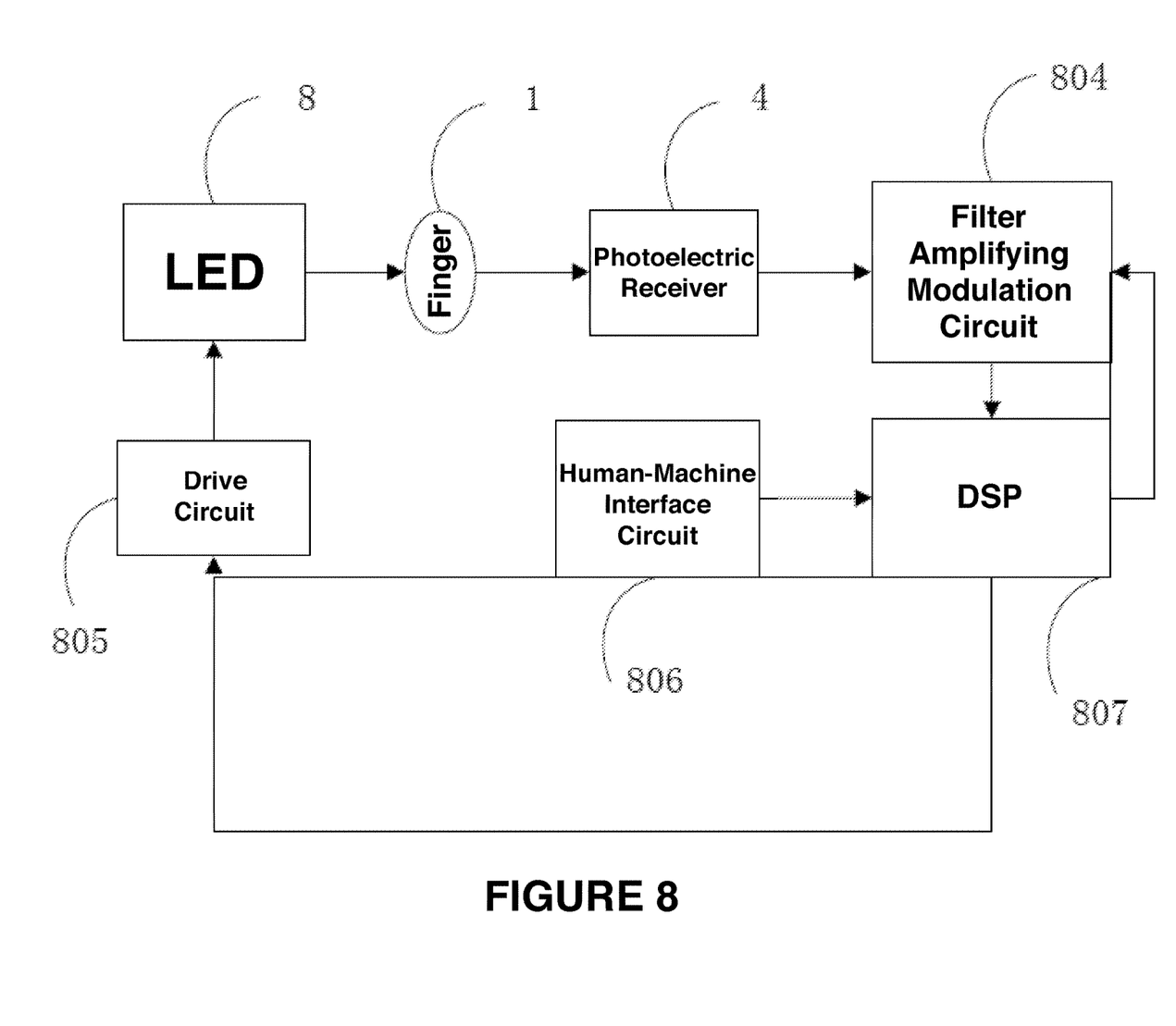
FIG. 8 is a detection flowchart.

FIG. 8 is a detection flowchart.

The photoelectric LED probe consists of a light-emitting diode 8 and a photoelectric receiver 4, containing four wavelengths (660 nm, 730 nm, 805 nm, 940 nm). The receiving scope of the photoelectric receiver 4 is within the scope of the four wavelengths, and the four wavelengths all are located within the wave bands in which the photoelectric receiver 4 has high conversion efficiency linearity. During measurement, after a human-machine interface 806 receives the operator order, DSP 807 generates a time sequence; a drive circuit 805 controls the light-emitting diode 8 to light up alternatively to radiate finger 1; the photoelectric receiver 4 receives the light transmitting trough finger 1; and a filter amplifying modulation circuit 804 converts a light signal into a current signal.

A non-invasive blood sugar measuring device based on the energy metabolic conservation of human body provided in the present invention comprises a finger end measuring probe, an exclusive communication cable, a main system instrument and supported mobile-phone-end healthy management software, which are connected in series. Wherein, the finger end measuring probe can obtain the environmental temperature and humidity, the temperature and humidity of the finger surface, the radiation temperature of the environment and finger, basal metabolic rate of the human body, degree of blood oxygen saturation, blood flow velocity, hemoglobin, heartbeat and other parameters. The main system instrument analyzes and processes those parameters to obtain the blood sugar value, and the blood sugar value can be displayed on the liquid crystal panel of the instrument and the healthy management software of the cell phone at the same time, wherein the healthy management software of the cell phone also has the functions of classification of individual data, drawing, and prompting, such that the user can comprehensively know the change of the blood sugar in a period of time.

The mobile-phone-end healthy management software in the non-invasive blood sugar measuring instrument together with the instrument completes the entire detection process, and conducts the functions of analysis of and management of the historical data of different users, so the historical data such as the blood sugar value, blood flow velocity and blood pressure of every user are dynamically represented to the user in graphic form. Thus, the user can know the change of the healthy conditions in a period of time.

The power supply and information transmission of the high-precision sensor portion are implemented through customized cables. The host is equipped with 2,800 mAh high-strength polymer lithium battery with over 10 d cruising ability in the standby state and over 8 h continuous detection time, completely meeting the daily use of the user. Besides the non-invasive blood sugar detection function, the host can also browse the historical detection and has a huge storage capability, providing data sources for the management on the daily blood sugar and cardiovascular data of the computer and the mobile-phone-end healthy management software. The data transmission to the computer and the mobile-phone-end healthy management software can proceed through USB or Bluetooth.

Figure 9:
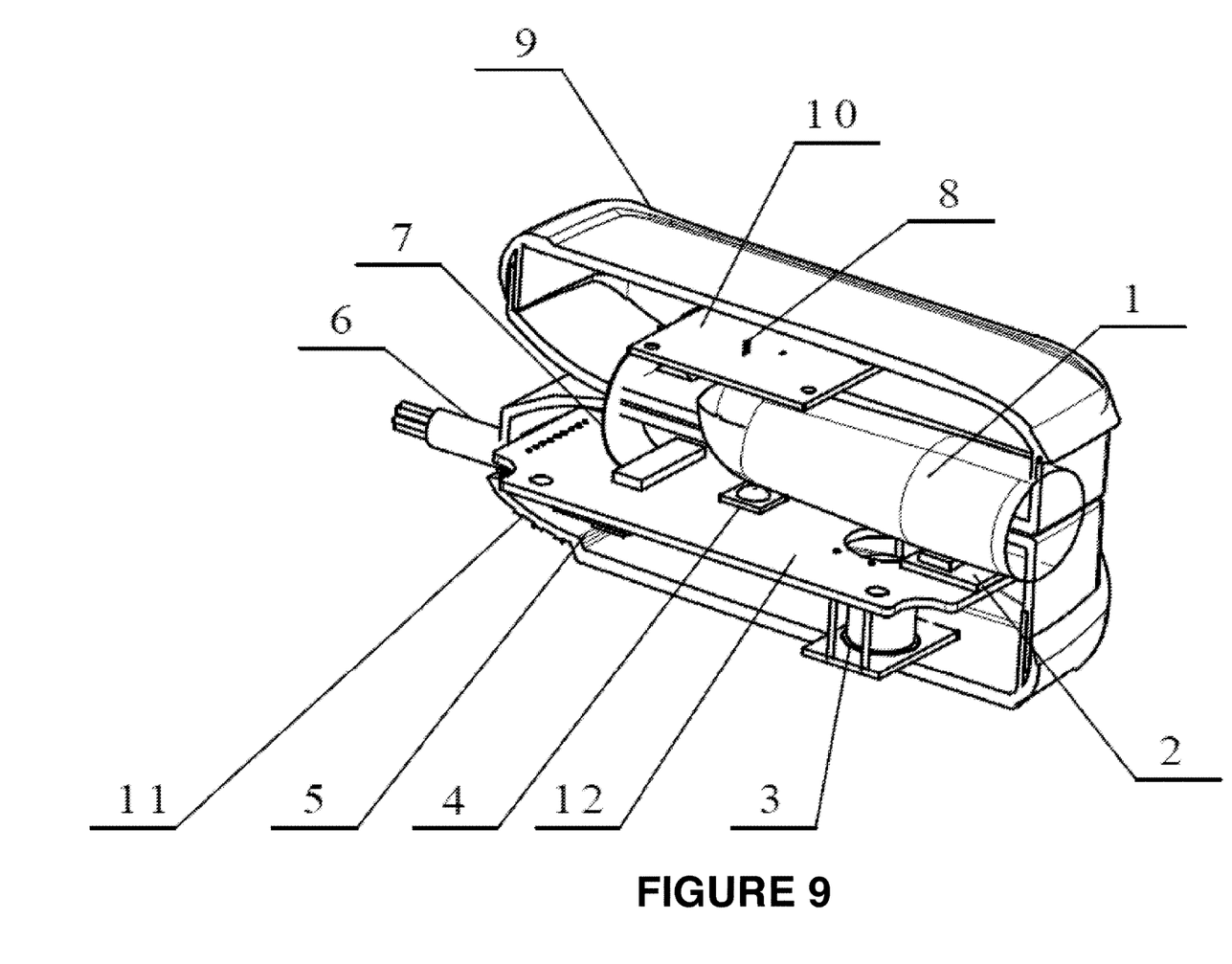
FIG. 9 is a structural view of the fingertip-measuring probe of the present invention.

FIG. 9 is a structural view of the fingertip-measuring probe of the present invention.

The fingertip measuring probe of the present invention comprises a finger surface temperature and humidity sensor 2, an upper holding portion 9, a lower holding portion 11, a radiation temperature sensor 3, a photoelectric receiver 4, an environmental temperature and humidity sensor 5, a communication cable 6, a connecting flat wire 7, a light-emitting diode 8, an upper holding portion 9, a first circuit board 10, a lower holding portion 11, and a second circuit board 12.

The upper holding portion 9 and the lower holding portion 11 work together to firmly hold the finger 1. The temperature-humidity sensor 2 is disposed at the upper surface of the second circuit board 12 for measuring the temperature and humidity on the finger surface. The radiation temperature sensor 3 is disposed at the lower surface of the second circuit board 12 for measuring the radiation temperature of the finger surface. The environmental temperature-humidity sensor 5 is disposed at the lower surface of the second circuit board 12 for measuring the environmental temperature and humidity. The photoelectric receiver 4 disposed at the upper surface of the second circuit board 12. The light-emitting diode 8 is disposed on the upper surface of the first circuit board 10. The light-emitting diode 8 emitting light rays which penetrate through the fingertip and then are received by the photoelectric receiver. The connecting flat wire 7 is connected the upper holding portion 9 and the lower holding portion 11. The communication cable 6 penetrates through the lower holding portion 11 is connected with the second circuit board 12.

Compared with the prior art, the non-invasive blood sugar measuring device of the present invention has a small and exquisite shape, is convenient and simple to operate, can realize non-invasive detection of the blood sugar value and a plurality of biological parameters of the human body, and reduces the pain of the patient except that caused by the diseases and the psychological burden during diagnosis and detection.

For the high-accuracy requirements for the energy information at the fingertip of the human body, the entire sensor portion employs the upper and lower holding portions with grooves. The upper and lower surfaces of the grooves are both covered with a layer of thermal insulating silicone gel to reduce the non-abnormal dissipation of heat caused by the external factors. The sensor is also a space three-dimensional structure inside, such that the environmental temperature and humidity sensor is less affected by the finger energy. The finger temperature and humidity sensor quickly and accurately reflect the temperature and humidity information on the finger surface, and the radiation temperature sensor can normally sense the heat radiated by the environment and finger. The basic biological parameter information of the human body obtained through the sensor includes environmental temperature, environmental humidity, finger surface temperature, finger surface humidity, environmental radiation temperature, finger radiation temperature, basal metabolic rate of the human body, degree of blood oxygen saturation, blood flow velocity, heartbeat, etc.

The non-invasive blood glucose measurement method disclosed in the present invention can be applied to non-invasive measurement of blood glucose, parameters related to energy metabolism of human body, healthy parameters of angiocarpy, etc.

This text gives some embodiments of the present invention, but those skilled in this field shall understand that embodiments in this text can be modified without departing from the spirit of the present invention. The above embodiments are only exemplary and shall not be regarded as limit in the protective scope of the present invention.

What is claimed is:

1. A non-invasive blood sugar measuring method, applied to non-invasive blood glucose measuring instruments including measuring hosts and fingertip measuring probes, said method comprising:
    pre-storing a random forest algorithm and a neural network prediction algorithm in the measuring host;
    measuring energy metabolism parameters of a fingertip of an individual to be measured and transmitting the parameters to the measuring host from the fingertip measuring probe;
    instructing the random forest algorithm to pre-measure the blood glucose type of the energy metabolism parameters of the fingertip of the individual to be measured and instructing a corresponding neural network prediction algorithm to calculate a blood glucose value of the fingertip of the individual to be measured by the measuring host.

2. The non-invasive blood sugar measuring method according to claim 1, wherein the random wrest algorithm is preset with a low blood sugar type, an intermediate blood sugar type and a high blood sugar type; the low blood sugar type corresponds to a low blood sugar eural network prediction algorithm; the intermediate blood sugar type corresponds to an intermediate blood sugar neural network prediction algorithm; and the high blood sugar type corresponds to a high blood sugar neural network prediction algorithm.

3. The non-invasive blood sugar measuring method according to claim 2, wherein before the step of pre-storing the random forest algorithm and the neural network prediction algorithm in the measuring host, said method comprises:
    measuring with the fingertip measuring probe the energy metabolism parameters of a plurality of individual fingertips to obtain specimen data of the plurality of individuals, each individual's specimen data containing different energy metabolism parameters of the fingertips thereof;
    employing the random forest algorithm through a computer to classify the specimen data of the plurality of individuals into low blood sugar type, intermediate blood sugar type and high blood sugar type; and
    defining the energy metabolism parameters in the specimen data of the low blood sugar type, intermediate blood sugar type and high blood sugar type as the input parameters of the original models of a non-invasive blood sugar value estimation system to obtain the low blood sugar neutral network prediction algorithm, intermediate blood sugar neutral network prediction algorithm and high blood sugar neutral network prediction algorithm.

4. The non-invasive blood sugar measuring, method according to claim 3, wherein the step of employing the random forest algorithm through a computer to classify the specimen data of the plurality of individuals into low blood sugar type, intermediate blood sugar type and high blood sugar type comprises:
  randomly selecting individual specimen data from the plurality of individual specimen data;
  splitting nodes of the selected individual specimen data and constructing a decision- making tree;
  repeating the splitting nodes step to construct a plurality of decision-making trees to generate random forests,
  voting the decision-making tree in the random forests, and according to the voting result, classifying the plurality of individual specimen data into the low blood sugar type, intermediate blood sugar type and high blood sugar type.

5. The non-invasive blood sugar measuring method according to claim 4, wherein the step of defining the energy metabolism parameters in the specimen data of the low blood sugar type, intermediate blood sugar type and high blood sugar type as the input parameters of the original models of the non-invasive blood sugar value estimation system to obtain the low blood sugar neutral network prediction algorithm, intermediate blood sugar neutral network prediction algorithm and high blood sugar neutral network prediction algorithm comprises:
  defining the enemy metabolism parameters in the specimen data of the low blood sugar type, intermediate blood sugar type and high blood sugar type as the input parameters of the corresponding neutral network;
  defining a minimally invasive blood sugar value as a calibration parameter and as the expected output value of the neutral network, and constructing an original model of a non-invasive blood sugar value estimation system;
  setting the specimen parameter data of the original model and initialize a weight and a threshold, calculating the output of the hidden layer and the output layer, defining the output of the output layer of each of the low blood sugar type, intermediate blood sugar type and high blood sugar type and the secondary error criteria function of the invasive blood sugar value as the control function, calculating the system's total error criteria function for the system to the plurality of training specimen data, gradually calculating the output error of nerve cells on each layer from the output layer, then adjusting the weight and threshold of the output layer and the hidden layer in accordance with an error gradient descent method, then calculating the error of all specimens according to the adjusted weight and threshold so that the final output value of the modified corresponding neutral system approaches the expected output value;
  stopping a learning cycle when the error of the output result is within the allowed scope or reaches the maximum learning times; otherwise, continuing to learning of a new cycle.

6. The non-invasive blood sugar measuring method according to claim 5, wherein the calculation formula of the original model is:

$$Y = purelin(T * tansig(W * X + \theta i)) + \theta_1,$$

X is the input parameter of the neutral network prediction algorithm; W and T are weights; $\theta_i$ and $\theta_1$ are thresholds; and Y is the final output value of the corresponding neutral network prediction algorithm.

7. The non-invasive blood sugar measuring method according to claim 6, wherein the calculation of the neutral network prediction algorithm is:

$$\begin{cases} Y_L = purelin(T_L * tansig(W_L * X_L + \theta_{iL})) + \theta_{1L} \\ Y_M = purelin(T_M * tansig(W_M * X_M + \theta_{iM})) + \theta_{1M} \\ Y_H = purelin(T_H * tansig(W_H * X_H + \theta_{iH})) + \theta_{1H} \end{cases}$$

XL, XM and XH are the input parameters of the low, intermediate and high blood sugar neutral network prediction algorithms, respectively; $W_L$, $W_M$, $W_H$, $T_L$, $T_M$, $T_H$ are the weights of the low, intermediate and high blood sugar neutral network prediction algorithms; $\theta_{1L}$, $\theta_{1M}$, $\theta_{1H}$ $\theta_{iL}$, $\theta_{iM}$, $\theta_{iH}$ are thresholds of the low, intermediate and high blood sugar neutral network prediction algorithms; $Y_L$, $Y_M$, $Y_H$ are the final output values of the low, intermediate and high blood sugar neutral network prediction algorithms.

8. The non-invasive blood sugar measuring method according to claim 7, wherein the step of measuring the energy metabolism parameters of the fingertip of the individual to be measured and transmitting the parameters to the measuring host by the fingertip measuring probe comprises:
  measuring with the fingertip measuring probe the temperature difference between the fingertip surface and the environment, the humidity difference, the radiation temperature difference between the fingertip surface and the environment, the blood oxygen saturation difference of the fingertip, the blood flow velocity, and the pulse rate value;
  calculating with the fingertip measuring probe said temperature difference between the fingertip surface and the environment, said humidity difference and said radiation temperature difference between the fingertip surface and the environment to obtain a basic metabolism rate;
  transmitting from the fingertip measuring probe the energy metabolism parameters including said temperature difference between the fingertip surface and the environment, said humidity difference, said radiation temperature difference between the fingertip surface and the environment and said basic metabolism rate to the measuring host.

9. The non-invasive blood sugar measuring method according to claim 8, wherein the step of calling the random forest algorithm to predict the blood sugar type of the energy metabolism parameter of the fingertip of the individual to be measured and calling the corresponding neutral network prediction algorithm to calculate the blood sugar value of the fingertip of the individual to be measured by the measuring host comprises:
  calling a plurality of decision-making tree models in the constructed random forest algorithm to judge the blood sugar type of the energy metabolism parameter;
  classifying the individual specimen data into the low blood sugar type, or intermediate blood sugar type or high blood sugar type, according to the voting result of every decision-making tree and in accordance with the principle that the minority is subordinate to the majority;

calling the corresponding neutral network prediction algorithm pre-stored in the host to calculate and obtain the invasive blood sugar value of the fingertip of the individual to be measured, according to the classification result.

\* \* \* \* \*